(12) United States Patent
Rao et al.

(10) Patent No.: US 11,001,825 B2
(45) Date of Patent: May 11, 2021

(54) THERMOPHILIC L-ASPARAGINASE MUTANT AND SCREENING AND FERMENTATION METHODS THEREOF

(71) Applicant: Jiangnan University, Wuxi (CN)

(72) Inventors: Zhiming Rao, Wuxi (CN); Xu Li, Wuxi (CN); Xian Zhang, Wuxi (CN); Shuqin Xu, Wuxi (CN); Jingyi Hu, Wuxi (CN); Meijuan Xu, Wuxi (CN); Taowei Yang, Wuxi (CN)

(73) Assignee: Jiangnan University, Wuxi (CN)

( * ) Notice: Subject to any disclaimer, the term of this patent is extended or adjusted under 35 U.S.C. 154(b) by 106 days.

(21) Appl. No.: 16/255,973

(22) Filed: Jan. 24, 2019

(65) Prior Publication Data

US 2019/0185840 A1 Jun. 20, 2019

Related U.S. Application Data

(63) Continuation of application No. PCT/CN2017/116568, filed on Dec. 15, 2017.

(51) Int. Cl.
*C12N 9/82* (2006.01)
*C12P 13/20* (2006.01)
*C12N 15/75* (2006.01)
*C12Q 1/34* (2006.01)

(52) U.S. Cl.
CPC ............ *C12N 9/82* (2013.01); *C12N 15/75* (2013.01); *C12P 13/20* (2013.01); *C12Q 1/34* (2013.01); *C12Y 305/01001* (2013.01)

(58) Field of Classification Search
CPC . C12N 9/82; C12N 15/75; C12P 13/20; C12P 3/00; C12Q 1/34; C12Y 305/01001
See application file for complete search history.

(56) References Cited

U.S. PATENT DOCUMENTS

2014/0256002 A1* 9/2014 Shin ............... C12Y 305/01001
435/109

FOREIGN PATENT DOCUMENTS

| CN | 104146270 A | 11/2014 |
|----|-------------|---------|
| CN | 104371993 A | 2/2015 |
| CN | 105062997 A | 11/2015 |
| WO | 2014170811 A2 | 10/2014 |

* cited by examiner

*Primary Examiner* — Paul J Holland
(74) *Attorney, Agent, or Firm* — IPro, PLLC

(57) ABSTRACT

The present disclosure discloses a thermophilic L-asparaginase mutant and screening and fermentation methods thereof, and belongs to the field of gene engineering, enzyme engineering and fermentation engineering. In *Bacillus subtilis* 168, a *Pyrococcus yayanosii* CH1-derived L-asparaginase encoding gene is used as a template, and a mutation library is constructed by an error-prone PCR (epPCR) technology. A mutant strain with improved specific enzyme activity is screened through a high-flux screening method of synchronous cell disruption and enzyme activity measurement. Mutated residues included in a positive mutant are analyzed to construct a composite mutant strain S17G/A90S/R156S/K272A with improved specific enzyme activity and specific enzyme activity of 3108 U/mg. An expression quantity of the composite mutant strain in the *Bacillus subtilis* 168 is increased through measures of a strong promoter $P_{43}$ and RBS optimization. Finally, the *Bacillus subtilis* 168 with a gene of the L-asparaginase composite mutant strain is subjected to enzyme production fermentation in a 5 L fermentation tank through culture medium optimization and pH and feeding coupling strategies. The enzyme activity yield of the L-asparaginase is up to 6453+/−127 U/mL.

5 Claims, No Drawings
Specification includes a Sequence Listing.

THERMOPHILIC L-ASPARAGINASE MUTANT AND SCREENING AND FERMENTATION METHODS THEREOF

TECHNICAL FIELD

The present disclosure relates to a thermophilic L-asparaginase mutant and screening and fermentation methods thereof, and belongs to the field of gene engineering, enzyme engineering and fermentation engineering.

BACKGROUND

L-asparaginase (E.C.3.5.1.1) can catalyze L-asparaginate to be deaminized to generate L-aspartic acid and ammonia. The L-asparaginase is mainly used in the pharmaceutical industry and the food industry. In the pharmaceutical industry, the L-asparaginase is used as one of therapeutic and anticancer drugs due to its inhibition effect on some tumors. L-asparaginase II separated and purified from *E. coli*, *Erwinia chrysanthemi* and *E. carotovora* has been widely applied to treating diseases such as acute lymphoblastic leukemia, lymphatic sarcoma and retothelial sarcoma. In the food industry, the L-asparaginase can reduce the content of the L-asparaginate which is a precursor substance of a cancerogenic substance, namely acrylamide, in food subjected to high-temperature treatment such as frying and baking, thereby reducing generation of the acrylamide from the source.

To obtain L-asparaginase which is more suitable for food and medical treatment, many researchers transform the L-asparaginase by measures of gene engineering, enzyme engineering and the like. Long et al. have found key amino acid residues that affect the activity of the L-asparaginase of *Bacillus subtilis*. By mutation of these residues, the catalytic efficiency of this enzyme is improved (Enzyme Microb Technol, 82, 15-22). Offman et al. have obtained a mutant strain which is capable of resisting protease hydrolysis and has improved enzyme activity by building a new genetic algorithm and researching the partial flexibility and the molecular dynamics of the L-asparaginase. The two characteristics are both characteristics required by medical L-asparaginase (Blood, 117(5), 1614-21). Kotzia and Labrou have obtained a mutant strain with improved enzyme activity and thermal stability by performing staggered extension hybridization on L-asparaginase genes of *E. carotovora* and *E. chrysanthemi* through orthogenesis. A beneficial screening method can simplify a screening process and reduce the workload. Although there are many measures for distinguishing key amino acids and constructing a mutation library, few methods for screening the L-asparaginase have been reported. In the aspect of screening of the L-asparaginase, there is only one method, reported by Gulati et al., for screening the L-asparaginase on a flat plate by taking L-asparaginate as a unique carbon source and taking phenol red as a developing agent (*Lett App Microbiol,* 24(I), 23-6), but this method is not applicable to screening of intracellular enzymes and thermophilic L-asparaginase.

In the aspect of a research for producing the L-asparaginase by microorganism fermentation, a few to several hundred (U/mL) of L-asparaginase is produced through fermentation of different processes and hosts. Ferrara et al. make *Saccharomyces cerevisiae*-derived L-asparaginase expressed in *Pichia pastoris*. Then, when a mycelium biomass is up to 107 g·L$^{-1}$ under high-density fermentation, an enzyme activity yield is up to 85.6 U/mL (Enzyme and Microbial Technology, 2006, 39(7): 1457-1463). Chityala et al. make *P. carotovorum* MTCC 1428-derived L-asparaginase expressed in *B. subtilis* WB800N, a final yield of the enzyme is up to 105 U/mL (Bioprocess and Biosystems Engineering. 2015. 38(11): 2271-2284) by optimizing conditions such as a culturing temperature, a rotating speed, a concentration of an inducer and inducing time and adopting a continuous inducing strategy. Feng et al. make *Bacillus subtilis*-derived L-asparaginase overexpressed in *Bacillus subtilis*, and the enzyme activity yield in a 3 L fermentation tank is finally up to 407.6 U/mL (Appl Microbiol Biotechnol, 101(4), 1509-1520) through measures of signal peptide screening, promoter mutation and protein nitrogen end excision, and is the previously reported highest enzyme activity yield of the L-asparaginase expressed in a safe food strain. Amardeep et al. feed through an exponential fed-batch strategy, control a specific growth rate of *E. coli* thalli, and optimize the adding time of an inducer IPTG. Finally, when OD$_{600}$ is 90, a yield of 870 U/mL of the L-asparaginase (Applied Microbiology and Biotechnology, 2005, 68(2): 189-197), which is the previously reported highest enzyme activity yield of the L-asparaginase is obtained. There are still rooms for improving the enzyme activity yield and the specific enzyme activity.

SUMMARY

To solve the above-mentioned problems, the present disclosure builds a screening method for synchronous cell disruption and enzyme activity measurement. A mutation library of L-asparaginase of *Pyrococcus yayanosii* CH1 is constructed by using an error-prone PCR (epPCR) technology, thus obtaining a positive mutant, and a composite mutant strain with improved enzyme activity through site-directed mutation. By use of promoter replacement and RBS optimization, an expression quantity of an enzyme in *Bacillus subtilis* 168 is increased. Finally, a gene of the composite mutant strain is efficiently fermented and produced through a culture medium optimization and pH and feeding coupling strategy.

A first objective of the present disclosure is to provide a thermophilic L-asparaginase mutant. An amino acid sequence of the mutant is SEQ ID NO.3 (S17G/E72D/N177D), SEQ ID NO.4 (A90S/I132L/R156S), SEQ ID NO.5 (L222V/K272A), SEQ ID NO.6 (S17G/W181F/K272A), SEQ ID NO.7 (S17G/A90S/R156S/V282S), SEQ ID NO.8 (R156S/K272A) or SEQ ID NO.9 (S17G/A90S/R156S/K272A).

A second objective of the present disclosure is to provide an encoding gene of the above-mentioned thermophilic L-asparaginase mutant.

A third objective of the present disclosure is to provide a recombinant expression vector containing the encoding gene of the above-mentioned thermophilic L-asparaginase mutant.

A fourth objective of the present disclosure is to provide a plasmid efficiently expressing the above-mentioned thermophilic L-asparaginase mutant. The plasmid is a recombinant expression plasmid obtained by linking the gene of the above-mentioned thermophilic L-asparaginase mutant between EcoR V and Hind III of pMA5 and linking a gene of a promoter P$_{43}$ of the sequence, as shown in SEQ ID NO.10, between the site EcoR I and the site EcoR V of the pMA5.

In one implementation mode of the present disclosure, the plasmid is that an RBS sequence included in the promoter P$_{43}$ is replaced with an RBS sequence, as shown in SEQ ID NO.11, of a nucleotide sequence.

A fifth objective of the present disclosure is to provide a genetically engineered bacterium expressing the above-mentioned thermophilic L-asparaginase mutant.

In one implementation mode of the present disclosure, the genetically engineered bacterium takes *Bacillus subtilis*, *Escherichia coli* or *saccharomycetes* as a host.

A sixth objective of the present disclosure is to provide a screening method of L-asparaginase. The method is applicable to screening of a thermophilic L-asparaginase mutant strain with high enzyme activity, and is implemented in a way of synchronous cell disruption and enzyme activity measurement.

In one implementation mode of the present disclosure, the screening method specifically includes: preheating a reaction solution (L-asparaginate, Tris-HCl, pH=7-9) in a baking oven with a temperature of 80 to 100° C. for 5 to 15 minutes; selecting a cultured mutation transformant single colony, inoculating the single colony into the preheated reaction solution, and heating the single colony in the baking oven with the temperature of 80 to 100° C. for 5 to 15 minutes; and adding a Nessler reagent for development, placing the single colony at a room temperature for 2 to 5 minutes, and measuring an absorbancy of the developed solution with an ELIASA under the condition of $OD_{450}$.

In one implementation mode of the present disclosure, the screening method is used for screening the mutant according to claim 1.

A seventh objective of the present disclosure is to provide a fermentation method of the above-mentioned thermophilic L-asparaginase mutant. The method specifically includes: inoculating the thermophilic L-asparaginase mutant into a fermentation culture medium according to an inoculation amount of 5 to 10 percent, respectively linking a feeding culture medium and ammonia water at a concentration of 40 to 60 percent to acid and alkali inlets of a fermentation tank under fermentation conditions of 500 to 700 rpm and 2 to 6 vvm, setting the pH to 7, and feeding when the pH is more than 7.

In one implementation mode of the present disclosure, the fermentation culture medium is prepared from constituents of 45 to 50 g/L glycerol, 30 to 40 g/L peptone, 1 to 2 g/L ammonia chloride, 10 to 20 g/L maize slurry, 2.5 to 3 g/L $K_2HPO_4$, 2 to 2.5 g/L $KH_2PO_4$ 1.5 to 2 g/L $MgSO_4.7H_2O$ and 5 to 10 g/L NaCl, and the pH is adjusted to 7.

In one implementation mode of the present disclosure, the feeding culture medium is prepared from constituents of 40 to 60 percent of glycerol and 7 to 8 percent of yeast powder.

An eighth objective of the present disclosure is to provide application of the thermophilic L-asparaginase mutant in food and medical industries.

The present disclosure has the beneficial effects that:

A high-flux screening method suitable for thermophilic L-asparaginase is provided. The cell disruption and the enzyme activity measurement are synchronously performed at a high temperature, so that the problem that intracellular enzymes and thermophilic enzymes are difficult to screen is solved.

The composite mutant strain is obtained, and has the specific enzyme activity up to 3108 U/g which is 2.1 times the original enzyme.

The recombinant strain highly expressing the L-asparaginase is obtained through the promoter screening and the RBS optimization.

The present disclosure realizes high-yield fermentation of the L-asparaginase in a 5 L fermentation tank, and the enzyme activity yield is up to 6453 U/mL which is much higher than the reported highest enzyme activity yield.

DETAILED DESCRIPTION

For the purpose of understanding technical contents of the present disclosure more clearly, a detailed description is made by taking the following embodiments for example to only better understand the contents of the present disclosure instead of limiting the protection scope of the present disclosure.

A starting culture medium is prepared from: 35 g/L saccharose, 15 g/L peptone, 0.8 g/L urea, 12 g/L maize slurry, 2.612 g/L $K_2HPO_4$ and 2.041 g/L $KH_2PO_4$.

A fermentation culture medium is prepared from: 47 g/L glycerol, 35 g/L peptone, 1.5 g/L ammonia chloride, 15 g/L maize slurry, 2.612 g/L $K_2HPO_4$, 2.041 g/L $K_2HPO_4$, 1.845 g/L $MgSO_4.7H_2O$ and 5 g/L NaCl, and the pH is adjusted to 7 with NaOH.

A feeding culture medium is prepared from: 50 percent of glycerol and 7.5 percent of yeast powder.

EXAMPLE 1

Construction, Transformation and Expression of Recombinant Plasmid pMA5-Asnase (1) For an L-asparaginase encoding gene sequence deduced from *Pyrococcus yayanosii* CH1, the homology between this sequence and *Escherichia coli*-derived L-asparaginase is 24.34 percent. The homology between this sequence and *Bacillus subtilis*-derived L-asparaginase is 20.41 percent. The homology between this sequence and *Thermococcus kodakarensis*-derived L-asparaginase is 65.15 percent. According to the L-asparaginase encoding gene sequence (SEQ ID NO.1) deduced from *Pyrococcus yayanosii* CH1, Sangon Biotech (Shanghai) Co., Ltd. is entrusted to optimize an L-asparaginase gene, then to clone the gene onto a vector pUCk to form a template (SEQ ID NO.2), and to design primers for PCR amplification. A gel extraction kit is adopted to purify and recycle PCR products, and the concentration of the recycled products is detected through electrophoresis. The recycled products are stored in a 1.5 ml centrifugal tube which is then put into a refrigerator for storage and later use.

(2) The recycled products obtained in Step (1) and a pMA5 plasmid are respectively subjected to double enzyme digestion with BamH I and Mlu I at 37° C. for 40 minutes. Products are recycled with the gel extraction kit. The recycled products are linked. A linkage system includes: 7 ul of enzyme-digested products of a target gene, 1 uL of enzyme-digested products of pMA5, 1 uL of T4 link ligase buffer and 1 uL of T4 link ligase, and enzyme linking is carried out at 16° C. for 12 hours. The linked products are transferred into a competence of *Bacillus subtilis* 168, a kanamycin resistant plate of LB is coated for culturing for 12 hours. A positive gene is selected and cloned to a 10 mL LB shake flask for culturing to extract a plasmid for double enzyme digestion verification. After the verification is succeeded, the gene is sent to Sangon Biotech (Shanghai) Co., Ltd. for sequencing. After the sequence is correct, the plasmid pMA5-asnase is constructed, which is stored at −20° C. The recombinant strain corresponding to the pMA5-asnase is a recombinant strain *B. subtilis* 168/pMA5-asnase. A bacterium solution is added into glycerol till the concentration is 15 percent. The solution is put into a refrigerator at −40° C. for storage and later use.

(3) The recombinant strain *B. subtilis* 168/pMA5-asnase constructed in Step (2) is inoculated into the 10 mL LB shake flask for culturing for 12 hours, and then is transferred into a 100 mL starting culture medium for culturing for 24 hours. An enzyme activity of fermented supernate is measured by a Nessler developing method (Enzyme Microb Technol, 82, 15-22), thus obtaining an extracellular enzyme activity. B. subtilis 168/pMA5-asnase fermented bacteria are collected. Cells are disrupted by ultrasonic waves. Supernate obtained by centrifugating the disrupted cells is taken, and the enzyme activity of the supernate is measured by the Nessler developing method, thus obtaining an intracellular enzyme activity. The unit of the enzyme activity is defined as follows: under the measurement conditions, an enzyme amount required for producing 1 umol of ammonia gas within every minute is 1 enzyme activity unit. After the B. subtilis 168/pMA5-asnase is cultured for 24 hours, the total enzyme activity of the L-asparaginase expressed by the B. subtilis 168/pMA5-asnase is up to 89.03+/−7.3 U/mL (the extracellular enzyme activity and the intracellular enzyme activity are respectively 23.31 and 65.72 U/mL). Intracellular enzyme protein is purified by a nickel column affinity chromatography method. After the intracellular enzyme protein is purified, it is measured that an optimum temperature for this enzyme is 95° C. The concentration of the protein is measured by a Bradford method, thus obtaining that the specific enzyme activity of Pyrococcus yayanosii CH1 is 1483 U/mL.

EXAMPLE 2

Screening, Construction and Expression of Mutant Strain with High Enzyme Activity (1) The pMA5-asnase is used as a template. Primers are designed for epPCR by using a GeneMorph II random mutagenesis kit. Products obtained by epPCR amplification are linked into sites BamHI and MluI of pMA5, and then are transformed into Bacillus subtilis 168. A kanamycin resistant plate of LB is coated for culturing for 12 hours.

(2) In a baking oven (with no air) at 95° C., a 96-deep-well plate (with a cover) filled with 0.5 mL of reaction solution (25 mML-asparaginate, 50 Mm Tris-HCl, pH=8) is preheated for 10 minutes. A full loop of cultured mutation transformant single colonies which are cultured for 12 hours and obtained in Step (1) is selected with an inoculation loop, and is inoculated into the preheated 96-deep-well plate filled with the reaction solution. The single colony in the baking oven (with no air) at 95° C. is heated for 10 minutes. 10 uL of Nessler reagent is added for development. After placement at a room temperature for 3 minutes, 200 ul of the developed solution is put into the 96-well plate to measure an absorbancy with an ELIASA under the condition of $OD_{450}$. The recombinant strain B. subtilis 168/pMA5-asnase containing the original Pyrococcus yayanosii CH1 L-asparaginase gene is used as a contrast. In the first round, three mutant strains (A1, B1 and C1) with relatively high L-asparaginase activity are selected from the colony, and then are cultured in LB for 12 hours. Plasmids are then extracted to obtain the most outstanding positive mutants A1(S17G/E72D/N177D), B1(A90S/I132L/R156S) and C1 (L222V/K272A). After the three mutated plasmids are mixed, a mixed plasmid is used as a template for epPCR amplification and screening in the second round. Three mutant strains (D2, E2 and F2) having the most outstanding effects are selected for sequencing again. In the second round of epPCR amplification and screening, three most outstanding positive mutants D2(S17G/W181F/K272A), E2((S17G/A90S/R156S/V282S) and F2(R156S/K272A) are obtained.

(3) Amino acid sequences of the six mutant strains obtained in Step (2) are analyzed, and it is found that S17G, A90S, R156S and K272A are the most common mutations. The pMA5-asnase is used as a template, and primers are designed for overlap extension PCR step by step to introduce genes at the mutated sites S17G, A90S, R156S and K272A to a position between enzyme digestion sites BamH I and Mlu I of pMA5-asnase to construct a recombinant plasmid pMA5-S17G/A90S/R156S/K272A-2. The recombinant plasmid is transformed into the Bacillus subtilis 168 to form a recombinant expression strain B. subtilis 168/pMA5-S17G/A90S/R156S/K272A-2.

(4) The recombinant strain B. subtilis 168/pMA5-S17G/A90S/R156S/K272A-2 is subjected to shake-flask fermentation expression, purification and specific enzyme activity measurement according to the method in Step (3) of Embodiment 1. The enzyme activity yield of the B. subtilis 168/pMA5-S17G/A90S/R156S/K272A-2 is up to 178.16+/−15.6 U/mL (the extracellular enzyme activity and the intracellular enzyme activity are respectively 129.95 and 48.21 U/mL), which is twice that of the original strain. Furthermore, it is measured that the specific enzyme activity of the mutant S17G/A90S/R156S/K272A is 3108+/−152 U/mg, which is 2.1 times that of the original enzyme.

EXAMPLE 3

Construction of High-Yield L-Asparaginase Recombinant Strain (1) The pMA5-S17G/A90S/R156S/K272A-2 is used as a template, and primers are designed for PCR amplification. PCR products are linked between enzyme digestion sites Ecor V and Hind III of pMA5 in the way in Step (2) of Embodiment 1 to construct a recombinant plasmid pMA5-S17G/A90S/R156S/K272A. The recombinant plasmid is put into a refrigerator at −20° C. for storage and later use.

(2) A genome of Bacillus subtilis 168 is extracted and used as a template. Primers are designed for PCR amplification, and obtained products are respectively linked between enzyme digestion sites EcoRI and EcoRV of the pMA5-S17G/A90S/R156S/K272A in the way in Step (2) of Embodiment 1 to construct recombinant plasmids pMA5-$P_{43}$-S17G/A90S/R156S/K272A (the sequence of the promoter $P_{43}$ is as shown in SEQ ID NO.10), pMA5-$P_{groEs}$-S17G/A90S/R156S/K272A, pMA5-$P_{sigX}$-S17G/A90S/R156S/K272, pMA5-$P_{trnQ}$-S17G/A90S/R156S/K272A and pMA5-$P_{yxiE}$-S17G/A90S/R156S/K272A which have different promoters. The five plasmids are respectively transferred into the Bacillus subtilis 168. The five recombinant strains are subjected to shake-flask fermentation expression according to the method in Step (3) of Embodiment 1. The expression quantity of the recombinant strain B. subtilis 168/pMA5-$P_{43}$-S17G/A90S/R156S/K272A containing the promoter $P_{43}$ is 0.53 time greater than that of the contrast B. subtilis 168/pMA5-S17G/A90S/R156S/K272A-2, and the enzyme activity of the recombinant strain is 270.8+/−31 U/mL (the extracellular enzyme activity and the intracellular enzyme activity are respectively 205.42 and 65.32 U/mL).

(3) An RBS sequence suitable for P43 and L-asparaginase transcription is designed by using an RBS calculator (https://www.denovodna.com/software/doLogin). The designed RBS sequence (SEQ ID NO. 11) replaces the original RBS sequence of P43 in a manner of long-primer PCR. The pMA5-P43-S17G/A90S/R156S/K272A is used as a template, and primers are designed for PCR. Obtained products are respectively linked between enzyme digestion sites EcoRI and EcoRV of the pMA5-S17G/A90S/R156S/K272A in the way in Step (2) of Embodiment 1 to construct a recombinant plasmid pMA5-P43-S17G/A90S/R156S/K272A. The plasmid is transferred into the Bacillus subtilis 168 to form a recombinant strain B. subtilis 168/pMA5-P43-RBS-S17G/A90S/R156S/K272A. The obtained recombinant strain is subjected to shake-flask fermentation expression according to the method in Step (3) of Embodiment 1, thus obtaining the enzyme activity of 383.5+/−1 U/mL (the extracellular enzyme activity and the intracellular enzyme activity are respectively 285.65 and 97.85 U/mL).

EXAMPLE 4

Production of L-Asparaginate by Fermentation of L-Asparaginase in 5 L Fermentation Tank By taking the enzyme activity yield as a target and the recombinant strain B. subtilis 168/pMA5-$P_{43}$-RBS-S17G/A90S/R156S/K272A as an expression strain, in the 5 L fermentation tank, a feeding culture medium (50 percent of glycerol and 7.5 percent of yeast powder) and ammonia water at the concentration of 50 percent are respectively linked to acid and alkali inlets of the fermentation tank, and the pH is set to 7. Feeding is automatically carried out when the pH is more than 7, thereby realizing a pH and feeding coupling fermentation strategy. The cryopreserved B. subtilis 168/pMA5-$P_{43}$-RBS-S17G/A90S/R156S/K272A is inoculated into a 10 mL LB culture medium for shake-flask culturing for 12 hours, and then is transferred into a 100 mL of LB culture medium for shake-flask culturing for 12 hours. The B. subtilis 168/pMA5-$P_{43}$-RBS-S17G/A90S/R156S/K272A is inoculated into the 5 L fermentation tank filled with a 2 L fermentation culture medium according to an inoculation amount of 5 percent, so as to perform fermentation at a ventilating amount of 4 vvm at 600 rpm through the pH and feeding coupling strategy.

The recombinant strain B. subtilis 168/pMA5-$P_{43}$-RBS-S17G/A90S/R156S/K272A constructed in Step (3) of Embodiment 3 is used as an expression strain, and the enzyme activity yield of the L-asparaginase of the strain is used as a research object, so that constituents and concentrations of a carbon source, a nitrogen source, an inorganic nitrogen source and maize slurry in a starting culture medium are subjected to single factor and orthogonal experiments, thus obtaining a fermentation culture medium which is prepared from 47 g/L glycerol, 35 g/L peptone, 1.5 g/L ammonia chloride, 15 g/L maize slurry, 2.612 g/L $K_2HPO_4$, 2.041 g/L $K_2HPO_4$, 1.845 g/L $MgSO_4.7H_2O$ and 5 g/L NaCl, and the pH is adjusted to 7 with NaOH.

The feeding culture medium is prepared from 50 percent of glycerol and 7.5 percent of yeast powder.

The recombinant strain B. subtilis 168/pMA5-$P_{43}$-RBS-S17G/A90S/R156S/K272A constructed in Step (3) of Embodiment 3 is subjected to LB plate streak culturing for 12 hours, and a single colony is inoculated into the 10 mL LB for shake-flask culturing at 37° C. and 180 rpm for 12 hours. 500 uL of strain solution is inoculated into the 100 mL LB for shake-flask culturing at 37° C. and 180 rpm for 12 hours. The strain is inoculated into the 5 L fermentation tank filled with the 2 L of fermentation culture medium according to an inoculation amount of 5 percent. In the 5 L fermentation tank, the feeding culture medium and the ammonia water at the concentration of 50 percent are respectively linked to the acid and alkali inlets of the fermentation tank, and the pH is set to 7. Feeding is automatically carried when the pH is more than 7. The fermentation is performed by adopting the pH and feeding coupling fermentation strategy. Sampling is performed every 3 to 6 hours to monitor fermentation condition. After fermentation for 36 hours, the highest enzyme activity yield is 6453+/−127 U/mL.

EXAMPLE 5

Production of Enzyme Through Fermentation of L-Asparaginase Recombinant Strain Under Other Fermentation Strategies The L-asparaginase recombinant strain constructed in Embodiment 3 is fermented to produce the enzyme under an L-asparaginase fermentation strategy described in the document (Bioprocess and Biosystems Engineering, 2015, 38(11): 2271-2284), and the highest enzyme activity of L-asparaginase is up to 317+/−53 U/mL.

The L-asparaginase recombinant strain constructed in Embodiment 3 is fermented to produce the enzyme under an L-asparaginase fermentation strategy described in the document (Applied Microbiology and Biotechnology, 2005, 68(2): 189-197), and the highest enzyme activity of L-asparaginase is up to 1352+/−87 U/mL.

What is claimed is:

1. A thermophilic L-asparaginase mutant, wherein said thermophilic L-asparaginase mutant comprises the amino acid sequence set forth in SEQ ID NO: 3, SEQ ID NO: 4, SEQ ID NO: 5, SEQ ID NO: 6, SEQ ID NO: 7, SEQ ID NO: 8, or SEQ ID NO: 9, and wherein said thermophilic L-asparaginase mutant possesses asparaginase enzyme activity.

2. A fermentation method, comprising:
  inoculating the thermophilic L-asparaginase mutant of claim 1 into a fermentation culture medium in an inoculation amount of 5 to 10 percent,
  linking a feeding culture medium and ammonia water at a concentration of 40 to 60 percent to acid and alkali inlets of a fermentation tank under fermentation conditions of 500 to 700 rpm and 2 to 6 vvm,
  setting pH to 7, and
  feeding when the pH is more than 7.

3. The fermentation method of claim 2, wherein the fermentation culture medium comprises 45 to 50 g/L glycerol, 30 to 40 g/L peptone, 1 to 2 g/L ammonia chloride, 10 to 20 g/L maize slurry, 2.5 to 3 g/L $K_2HPO_4$, 2 to 2.5 g/L $KH_2PO_4$, 1.5 to 2 g/L $MgSO_4*7H_2O$, and 5 to 10 g/L NaCl, and with a pH adjusted to 7.

4. The fermentation method of claim 2, wherein the feeding culture medium comprises 40 to 60 percent glycerol and 7 to 8 percent yeast powder.

5. The thermophilic L-asparaginase mutant of claim 1, wherein the asparaginase enzyme activity of the thermophilic L-asparaginase is greater than wild-type thermophilic L-asparaginase activity measured under identical conditions.

* * * * *

SEQUENCE LISTING

```
<160> NUMBER OF SEQ ID NOS: 11

<210> SEQ ID NO 1
<211> LENGTH: 987
<212> TYPE: DNA
<213> ORGANISM: Artificial Sequence
<220> FEATURE:
<223> OTHER INFORMATION: Synthetic DNA

<400> SEQUENCE: 1
atgagactgc tgatactggg gatgggaggg acgatagcca gcgttccgag cgaagaagga      60
tatgagagct ccctttccgt tgaggaaatc ctgaggctcg cgggccttga attaaagtgg     120
gaggtagaag ctagagacct tttgaacatt gacagcactc taatccagcc cgaggattgg     180
gttctgctag ctgagaccgt cttcgaggcc ttcgaggagt tcgatggggt ggtgattacc     240
catggaaccg atacgctggc ttacacagcc tccatgctga gcttcatggt gaggaaccct     300
```

```
cccgtgccga tagtcctgac gggggcaatg aggcccatca cagagccggg cagcgatgcg      360
ccaaggaact tgtggaccgc cttgaggttc gctatagaag tgttccgggg ggtttacgtg      420
gccttcatgg ataaagtcat gctgggcgtg agggtctcta aggtgagggc tgtaggtctt      480
aacgcctttc agagcataaa ctatccagac atcgcctacg taaagggcaa caggattcac      540
tggaatgcta aacctcccaa actagagggg gagcccgttc ttgacacgcg tcatgagcca      600
agggttctcg tcctcaggct cgttccgggg atggaggggg acgtgctgga agccgccctt      660
gagctcgggt acaggggat agtcctcgag ggatacgggg ttggtggaat tccctataga       720
ggtagggacc tccttgatgt ggtgagaaga gtggcaacgg aaattccggt cgtaatgacg      780
acccagactc tctatgatgg tgttgacctg acgaagtaca agttggcag aaaggccttg       840 gaggtgggcg tcatacccgc gggagacatg acgaaggaag ccacaattac taagctcatg      900
tggatcctcg gccacacgag ggacgtagga gaggtaagga ggcttatgct gactaatatg      960
gtgggagaaa taggaaaatc agcgtag                                         987

<210> SEQ ID NO 2
<211> LENGTH: 987
<212> TYPE: DNA
<213> ORGANISM: Artificial Sequence
<220> FEATURE:
<223> OTHER INFORMATION: Synthetic DNA

<400> SEQUENCE: 2
atgagactgc tgatcctggg aatgggagga acaatcgcaa gtgtgccttc agaagaggga       60
tacgaatcat cactgtctgt ggaggagatc ctgagacttg caggacttga gctgaagtgg      120
gaagttgagg ctagagatct gctgaacatc gattctacgt tgatccagcc tgaggattgg      180
gttctgctgg ctgaaacagt attcgaggca ttcgaggaat ttgacggagt ggtaataacc      240
cacggtacag acacgctcgc ttacacagct tcgatgctta gctttatggt gagaaaccct      300
cctgtgccta tcgtactcac gggagcaatg aggcctatta cagagccagg ttccgatgca      360
ccaaggaact tatggacagc tttgagattt gctatcgaag gagtgccagg agtttacgtg      420
gcctttatgg ataaggtcat gctcggagtg agagtaagca aggtccgtgc agttggtctt      480
aacgcctttc aaagcattaa ttatccagac atagcctatg tcaagggcaa tcgtattcat      540
tggaatgcca aaccgccgaa actcgaaggc gaaccggtgc tcgacacgcg acatgaaccg      600
cgtgttcttg tattgcgact tgttccgggt atggaaggcg atgtacttga agcggcctta      660
gaattgggtt atcgcggtat tgtccttgaa ggctatgggg tgggcgggat tccgtatcgt      720
ggccgcgatt tgcttgatgt tgttcggcgg gttgcgactg aaattccggt tgtaatgact      780
acacaaacat tatatgacgg cgttgacttg accaaataca agtcggccg aaagcgtta       840 gaagtcggcg tcattccggc gggggatatg actaaagaag cgaccattac gaaattaatg      900
tggatattag ccatacgcg cgatgtcggg gaagtccggc gcttaatgtt aaccaatatg      960
gtcggcgaaa ttgggaaatc cgcgtaa                                          987

<210> SEQ ID NO 3
<211> LENGTH: 328
<212> TYPE: PRT
<213> ORGANISM: Artificial Sequence
<220> FEATURE:
<223> OTHER INFORMATION: Protein translated from synthetic DNA

<400> SEQUENCE: 3
```

Met Arg Leu Leu Ile Leu Gly Met Gly Gly Thr Ile Ala Ser Val Pro
1               5                   10                  15

Gly Glu Glu Gly Tyr Glu Ser Ser Leu Ser Val Glu Glu Ile Leu Arg
            20                  25                  30

Leu Ala Gly Leu Glu Leu Lys Trp Glu Val Glu Ala Arg Asp Leu Leu
        35                  40                  45

Asn Ile Asp Ser Thr Leu Ile Gln Pro Glu Asp Trp Val Leu Leu Ala
50                  55                  60

Glu Thr Val Phe Glu Ala Phe Asp Glu Phe Asp Gly Val Val Ile Thr
65                  70                  75                  80

His Gly Thr Asp Thr Leu Ala Tyr Thr Ala Ser Met Leu Ser Phe Met
            85                  90                  95

Val Arg Asn Pro Pro Val Pro Ile Val Leu Thr Gly Ala Met Arg Pro
            100                 105                 110

Ile Thr Glu Pro Gly Ser Asp Ala Pro Arg Asn Leu Trp Thr Ala Leu
            115                 120                 125

Arg Phe Ala Ile Glu Gly Val Pro Gly Val Tyr Val Ala Phe Met Asp
130                 135                 140

Lys Val Met Leu Gly Val Arg Val Ser Lys Val Arg Ala Val Gly Leu
145                 150                 155                 160

Asn Ala Phe Gln Ser Ile Asn Tyr Pro Asp Ile Ala Tyr Val Lys Gly
            165                 170                 175

Asp Arg Ile His Trp Asn Ala Lys Pro Lys Leu Glu Gly Glu Pro
            180                 185                 190

Val Leu Asp Thr Arg His Glu Pro Arg Val Leu Val Leu Arg Leu Val
            195                 200                 205

Pro Gly Met Glu Gly Asp Val Leu Glu Ala Ala Leu Glu Leu Gly Tyr
            210                 215                 220

Arg Gly Ile Val Leu Glu Gly Tyr Gly Val Gly Gly Ile Pro Tyr Arg
225                 230                 235                 240

Gly Arg Asp Leu Leu Asp Val Val Arg Val Ala Thr Glu Ile Pro
                245                 250                 255

Val Val Met Thr Thr Gln Thr Leu Tyr Asp Gly Val Asp Leu Thr Lys
            260                 265                 270

Tyr Lys Val Gly Arg Lys Ala Leu Glu Val Gly Val Ile Pro Ala Gly
            275                 280                 285

Asp Met Thr Lys Glu Ala Thr Ile Thr Lys Leu Met Trp Ile Leu Gly
            290                 295                 300

His Thr Arg Asp Val Gly Glu Val Arg Arg Leu Met Leu Thr Asn Met
305                 310                 315                 320

Val Gly Glu Ile Gly Lys Ser Ala
                325

<210> SEQ ID NO 4
<211> LENGTH: 328
<212> TYPE: PRT
<213> ORGANISM: Artificial Sequence
<220> FEATURE:
<223> OTHER INFORMATION: Protein translated from synthetic DNA

<400> SEQUENCE: 4

Met Arg Leu Leu Ile Leu Gly Met Gly Gly Thr Ile Ala Ser Val Pro
1               5                   10                  15

Ser Glu Glu Gly Tyr Glu Ser Ser Leu Ser Val Glu Glu Ile Leu Arg
            20                  25                  30

```
Leu Ala Gly Leu Glu Leu Lys Trp Glu Val Glu Ala Arg Asp Leu Leu
        35                  40                  45

Asn Ile Asp Ser Thr Leu Ile Gln Pro Glu Asp Trp Val Leu Leu Ala
 50                  55                  60

Glu Thr Val Phe Glu Ala Phe Glu Glu Phe Asp Gly Val Val Ile Thr
 65                  70                  75                  80

His Gly Thr Asp Thr Leu Ala Tyr Thr Ser Ser Met Leu Ser Phe Met
                 85                  90                  95

Val Arg Asn Pro Pro Val Pro Ile Val Leu Thr Gly Ala Met Arg Pro
                100                 105                 110

Ile Thr Glu Pro Gly Ser Asp Ala Pro Arg Asn Leu Trp Thr Ala Leu
            115                 120                 125

Arg Phe Ala Leu Glu Gly Val Pro Gly Val Tyr Val Ala Phe Met Asp
130                 135                 140

Lys Val Met Leu Gly Val Arg Val Ser Lys Val Ser Ala Val Gly Leu
145                 150                 155                 160

Asn Ala Phe Gln Ser Ile Asn Tyr Pro Asp Ile Ala Tyr Val Lys Gly
                165                 170                 175

Asn Arg Ile His Trp Asn Ala Lys Pro Pro Lys Leu Glu Gly Glu Pro
            180                 185                 190

Val Leu Asp Thr Arg His Glu Pro Arg Val Leu Val Leu Arg Leu Val
        195                 200                 205

Pro Gly Met Glu Gly Asp Val Leu Glu Ala Ala Leu Glu Leu Gly Tyr
    210                 215                 220

Arg Gly Ile Val Leu Glu Gly Tyr Gly Val Gly Gly Ile Pro Tyr Arg
225                 230                 235                 240

Gly Arg Asp Leu Leu Asp Val Val Arg Arg Val Ala Thr Glu Ile Pro
                245                 250                 255

Val Val Met Thr Thr Gln Thr Leu Tyr Asp Gly Val Asp Leu Thr Lys
                260                 265                 270

Tyr Lys Val Gly Arg Lys Ala Leu Glu Val Gly Val Ile Pro Ala Gly
            275                 280                 285

Asp Met Thr Lys Glu Ala Thr Ile Thr Lys Leu Met Trp Ile Leu Gly
290                 295                 300

His Thr Arg Asp Val Gly Glu Val Arg Arg Leu Met Leu Thr Asn Met
305                 310                 315                 320

Val Gly Glu Ile Gly Lys Ser Ala
                325

<210> SEQ ID NO 5
<211> LENGTH: 328
<212> TYPE: PRT
<213> ORGANISM: Artificial Sequence
<220> FEATURE:
<223> OTHER INFORMATION: Protein translated from synthetic DNA

<400> SEQUENCE: 5

Met Arg Leu Leu Ile Leu Gly Met Gly Gly Thr Ile Ala Ser Val Pro
 1               5                  10                  15

Ser Glu Glu Gly Tyr Glu Ser Ser Leu Ser Val Glu Glu Ile Leu Arg
                20                  25                  30

Leu Ala Gly Leu Glu Leu Lys Trp Glu Val Glu Ala Arg Asp Leu Leu
            35                  40                  45

Asn Ile Asp Ser Thr Leu Ile Gln Pro Glu Asp Trp Val Leu Leu Ala
 50                  55                  60
```

Glu Thr Val Phe Glu Ala Phe Glu Glu Phe Asp Gly Val Val Ile Thr
65                  70                  75                  80

His Gly Thr Asp Thr Leu Ala Tyr Thr Ala Ser Met Leu Ser Phe Met
                85                  90                  95

Val Arg Asn Pro Pro Val Pro Ile Val Leu Thr Gly Ala Met Arg Pro
            100                 105                 110

Ile Thr Glu Pro Gly Ser Asp Ala Pro Arg Asn Leu Trp Thr Ala Leu
        115                 120                 125

Arg Phe Ala Ile Glu Gly Val Pro Gly Val Tyr Val Ala Phe Met Asp
    130                 135                 140

Lys Val Met Leu Gly Val Arg Val Ser Lys Val Arg Ala Val Gly Leu
145                 150                 155                 160

Asn Ala Phe Gln Ser Ile Asn Tyr Pro Asp Ile Ala Tyr Val Lys Gly
                165                 170                 175

Asn Arg Ile His Trp Asn Ala Lys Pro Pro Lys Leu Glu Gly Glu Pro
            180                 185                 190

Val Leu Asp Thr Arg His Glu Pro Arg Val Leu Val Leu Arg Leu Val
        195                 200                 205

Pro Gly Met Glu Gly Asp Val Leu Glu Ala Ala Leu Glu Val Gly Tyr
    210                 215                 220

Arg Gly Ile Val Leu Glu Gly Tyr Gly Val Gly Gly Ile Pro Tyr Arg
225                 230                 235                 240

Gly Arg Asp Leu Leu Asp Val Val Arg Val Ala Thr Glu Ile Pro
                245                 250                 255

Val Val Met Thr Thr Gln Thr Leu Tyr Asp Gly Val Asp Leu Thr Ala
            260                 265                 270

Tyr Lys Val Gly Arg Lys Ala Leu Glu Val Gly Val Ile Pro Ala Gly
        275                 280                 285

Asp Met Thr Lys Glu Ala Thr Ile Thr Lys Leu Met Trp Ile Leu Gly
    290                 295                 300

His Thr Arg Asp Val Gly Glu Val Arg Arg Leu Met Leu Thr Asn Met
305                 310                 315                 320

Val Gly Glu Ile Gly Lys Ser Ala
                325

<210> SEQ ID NO 6
<211> LENGTH: 328
<212> TYPE: PRT
<213> ORGANISM: Artificial Sequence
<220> FEATURE:
<223> OTHER INFORMATION: Protein translated from synthetic DNA

<400> SEQUENCE: 6

Met Arg Leu Leu Ile Leu Gly Met Gly Gly Thr Ile Ala Ser Val Pro
1               5                   10                  15

Gly Glu Glu Gly Tyr Glu Ser Ser Leu Ser Val Glu Glu Ile Leu Arg
            20                  25                  30

Leu Ala Gly Leu Glu Leu Lys Trp Glu Val Glu Ala Arg Asp Leu Leu
        35                  40                  45

Asn Ile Asp Ser Thr Leu Ile Gln Pro Glu Asp Trp Val Leu Leu Ala
    50                  55                  60

Glu Thr Val Phe Glu Ala Phe Glu Glu Phe Asp Gly Val Val Ile Thr
65                  70                  75                  80

His Gly Thr Asp Thr Leu Ala Tyr Thr Ala Ser Met Leu Ser Phe Met
                85                  90                  95

-continued

```
Val Arg Asn Pro Pro Val Pro Ile Val Leu Thr Gly Ala Met Arg Pro
            100                 105                 110

Ile Thr Glu Pro Gly Ser Asp Ala Pro Arg Asn Leu Trp Thr Ala Leu
        115                 120                 125

Arg Phe Ala Ile Glu Gly Val Pro Gly Val Tyr Val Ala Phe Met Asp
    130                 135                 140

Lys Val Met Leu Gly Val Arg Val Ser Lys Val Arg Ala Val Gly Leu
145                 150                 155                 160

Asn Ala Phe Gln Ser Ile Asn Tyr Pro Asp Ile Ala Tyr Val Lys Gly
                165                 170                 175

Asn Arg Ile His Phe Asn Ala Lys Pro Pro Lys Leu Glu Gly Glu Pro
            180                 185                 190

Val Leu Asp Thr Arg His Glu Pro Arg Val Leu Val Leu Arg Leu Val
        195                 200                 205

Pro Gly Met Glu Gly Asp Val Leu Glu Ala Ala Leu Glu Leu Gly Tyr
    210                 215                 220

Arg Gly Ile Val Leu Glu Gly Tyr Gly Val Gly Gly Ile Pro Tyr Arg
225                 230                 235                 240

Gly Arg Asp Leu Leu Asp Val Val Arg Val Ala Thr Glu Ile Pro
                245                 250                 255

Val Val Met Thr Thr Gln Thr Leu Tyr Asp Gly Val Asp Leu Thr Ala
                260                 265                 270

Tyr Lys Val Gly Arg Lys Ala Leu Glu Val Gly Val Ile Pro Ala Gly
                275                 280                 285

Asp Met Thr Lys Glu Ala Thr Ile Thr Lys Leu Met Trp Ile Leu Gly
            290                 295                 300

His Thr Arg Asp Val Gly Glu Val Arg Arg Leu Met Leu Thr Asn Met
305                 310                 315                 320

Val Gly Glu Ile Gly Lys Ser Ala
                325

<210> SEQ ID NO 7
<211> LENGTH: 328
<212> TYPE: PRT
<213> ORGANISM: Artificial Sequence
<220> FEATURE:
<223> OTHER INFORMATION: Protein translated from synthetic DNA

<400> SEQUENCE: 7

Met Arg Leu Leu Ile Leu Gly Met Gly Gly Thr Ile Ala Ser Val Pro
1               5                   10                  15

Gly Glu Glu Gly Tyr Glu Ser Ser Leu Ser Val Glu Gly Ile Leu Arg
                20                  25                  30

Leu Ala Gly Leu Glu Leu Lys Trp Glu Val Glu Ala Arg Asp Leu Leu
            35                  40                  45

Asn Ile Asp Ser Thr Leu Ile Gln Pro Glu Asp Trp Val Leu Leu Ala
        50                  55                  60

Glu Thr Val Phe Glu Ala Phe Glu Glu Phe Asp Gly Val Val Ile Thr
65                  70                  75                  80

His Gly Thr Asp Thr Leu Ala Tyr Thr Ser Ser Met Leu Ser Phe Met
                85                  90                  95

Val Arg Asn Pro Pro Val Pro Ile Val Leu Thr Gly Ala Met Arg Pro
            100                 105                 110

Ile Thr Glu Pro Gly Ser Asp Ala Pro Arg Asn Leu Trp Thr Ala Leu
        115                 120                 125
```

```
Arg Phe Ala Ile Glu Gly Val Pro Gly Val Tyr Val Ala Phe Met Asp
            130                 135                 140

Lys Val Met Leu Gly Val Arg Val Ser Lys Val Ser Ala Val Gly Leu
145                 150                 155                 160

Asn Ala Phe Gln Ser Ile Asn Tyr Pro Asp Ile Ala Tyr Val Lys Gly
                165                 170                 175

Asn Arg Ile His Trp Asn Ala Lys Pro Lys Leu Glu Gly Glu Pro
                180                 185                 190

Val Leu Asp Thr Arg His Glu Pro Arg Val Leu Val Leu Arg Leu Val
                195                 200                 205

Pro Gly Met Glu Gly Asp Val Leu Glu Ala Ala Leu Glu Leu Gly Tyr
            210                 215                 220

Arg Gly Ile Val Leu Glu Gly Tyr Gly Val Gly Ile Pro Tyr Arg
225                 230                 235                 240

Gly Arg Asp Leu Leu Asp Val Val Arg Val Ala Thr Glu Ile Pro
                245                 250                 255

Val Val Met Thr Thr Gln Thr Leu Tyr Asp Gly Val Asp Leu Thr Lys
                260                 265                 270

Tyr Lys Val Gly Arg Lys Ala Leu Glu Ser Gly Val Ile Pro Ala Gly
            275                 280                 285

Asp Met Thr Lys Glu Ala Thr Ile Thr Lys Leu Met Trp Ile Leu Gly
            290                 295                 300

His Thr Arg Asp Val Gly Val Arg Arg Leu Met Leu Thr Asn Met
305                 310                 315                 320

Val Gly Glu Ile Gly Lys Ser Ala
                325

<210> SEQ ID NO 8
<211> LENGTH: 328
<212> TYPE: PRT
<213> ORGANISM: Artificial Sequence
<220> FEATURE:
<223> OTHER INFORMATION: Protein translated from synthetic DNA

<400> SEQUENCE: 8

Met Arg Leu Leu Ile Leu Gly Met Gly Gly Thr Ile Ala Ser Val Pro
1               5                   10                  15

Ser Glu Glu Gly Tyr Glu Ser Ser Leu Ser Val Glu Glu Ile Leu Arg
                20                  25                  30

Leu Ala Gly Leu Glu Leu Lys Trp Glu Val Glu Ala Arg Asp Leu Leu
            35                  40                  45

Asn Ile Asp Ser Thr Leu Ile Gln Pro Glu Asp Trp Val Leu Leu Ala
        50                  55                  60

Glu Thr Val Phe Glu Ala Phe Glu Glu Phe Asp Gly Val Val Ile Thr
65                  70                  75                  80

His Gly Thr Asp Thr Leu Ala Tyr Thr Ala Ser Met Leu Ser Phe Met
                85                  90                  95

Val Arg Asn Pro Pro Val Pro Ile Val Leu Thr Gly Ala Met Arg Pro
                100                 105                 110

Ile Thr Glu Pro Gly Ser Asp Ala Pro Arg Asn Leu Trp Thr Ala Leu
            115                 120                 125

Arg Phe Ala Ile Glu Gly Val Pro Gly Val Tyr Val Ala Phe Met Asp
            130                 135                 140

Lys Val Met Leu Gly Val Arg Val Ser Lys Val Ser Ala Val Gly Leu
145                 150                 155                 160
```

Asn Ala Phe Gln Ser Ile Asn Tyr Pro Asp Ile Ala Tyr Val Lys Gly
                165                 170                 175

Asn Arg Ile His Trp Asn Ala Lys Pro Pro Lys Leu Glu Gly Glu Pro
            180                 185                 190

Val Leu Asp Thr Arg His Glu Pro Arg Val Leu Val Leu Arg Leu Val
            195                 200                 205

Pro Gly Met Glu Gly Asp Val Leu Glu Ala Ala Leu Glu Leu Gly Tyr
        210                 215                 220

Arg Gly Ile Val Leu Glu Gly Tyr Gly Val Gly Ile Pro Tyr Arg
225                 230                 235                 240

Gly Arg Asp Leu Leu Asp Val Val Arg Val Ala Thr Glu Ile Pro
                245                 250                 255

Val Val Met Thr Thr Gln Thr Leu Tyr Asp Gly Val Asp Leu Thr Ala
                260                 265                 270

Tyr Lys Val Gly Arg Lys Ala Leu Glu Val Gly Val Ile Pro Ala Gly
                275                 280                 285

Asp Met Thr Lys Glu Ala Thr Ile Thr Lys Leu Met Trp Ile Leu Gly
                290                 295                 300

His Thr Arg Asp Val Gly Glu Val Arg Arg Leu Met Leu Thr Asn Met
305                 310                 315                 320

Val Gly Glu Ile Gly Lys Ser Ala
                325

<210> SEQ ID NO 9
<211> LENGTH: 328
<212> TYPE: PRT
<213> ORGANISM: Artificial Sequence
<220> FEATURE:
<223> OTHER INFORMATION: Protein translated from synthetic DNA

<400> SEQUENCE: 9

Met Arg Leu Leu Ile Leu Gly Met Gly Gly Thr Ile Ala Ser Val Pro
1               5                   10                  15

Gly Glu Glu Gly Tyr Glu Ser Ser Leu Ser Val Glu Glu Ile Leu Arg
                20                  25                  30

Leu Ala Gly Leu Glu Leu Lys Trp Glu Val Glu Ala Arg Asp Leu Leu
            35                  40                  45

Asn Ile Asp Ser Thr Leu Ile Gln Pro Glu Asp Trp Val Leu Leu Ala
    50                  55                  60

Glu Thr Val Phe Glu Ala Phe Glu Glu Phe Asp Gly Val Val Ile Thr
65                  70                  75                  80

His Gly Thr Asp Thr Leu Ala Tyr Thr Ser Ser Met Leu Ser Phe Met
                85                  90                  95

Val Arg Asn Pro Pro Val Pro Ile Val Leu Thr Gly Ala Met Arg Pro
                100                 105                 110

Ile Thr Glu Pro Gly Ser Asp Ala Pro Arg Asn Leu Trp Thr Ala Leu
            115                 120                 125

Arg Phe Ala Ile Glu Gly Val Pro Gly Val Tyr Val Ala Phe Met Asp
    130                 135                 140

Lys Val Met Leu Gly Val Arg Val Ser Lys Val Ser Ala Val Gly Leu
145                 150                 155                 160

```
Asn Ala Phe Gln Ser Ile Asn Tyr Pro Asp Ile Ala Tyr Val Lys Gly
            165                 170                 175

Asn Arg Ile His Trp Asn Ala Lys Pro Pro Lys Leu Glu Gly Glu Pro
        180                 185                 190

Val Leu Asp Thr Arg His Glu Pro Arg Val Leu Val Leu Arg Leu Val
        195                 200                 205

Pro Gly Met Glu Gly Asp Val Leu Glu Ala Ala Leu Glu Leu Gly Tyr
        210                 215                 220

Arg Gly Ile Val Leu Glu Gly Tyr Gly Val Gly Gly Ile Pro Tyr Arg
225                 230                 235                 240

Gly Arg Asp Leu Leu Asp Val Val Arg Val Ala Thr Glu Ile Pro
            245                 250                 255

Val Val Met Thr Thr Gln Thr Leu Tyr Asp Gly Val Asp Leu Thr Ala
            260                 265                 270

Tyr Lys Val Gly Arg Lys Ala Leu Glu Val Gly Val Ile Pro Ala Gly
            275                 280                 285

Asp Met Thr Lys Glu Ala Thr Ile Thr Lys Leu Met Trp Ile Leu Gly
            290                 295                 300

His Thr Arg Asp Val Gly Glu Val Arg Arg Leu Met Leu Thr Asn Met
305                 310                 315                 320

Val Gly Glu Ile Gly Lys Ser Ala
                325

<210> SEQ ID NO 10
<211> LENGTH: 300
<212> TYPE: DNA
<213> ORGANISM: Artificial Sequence
<220> FEATURE:
<223> OTHER INFORMATION: Synthetic DNA

<400> SEQUENCE: 10
tgataggtgg tatgttttcg cttgaactt taaatacagc cattgaacat acggttgatt      60
taataactga caaacatcac cctcttgcta aagcggccaa ggacgctgcc gccggggctg    120
tttgcgtttt tgccgtgatt tcgtgtatca ttggtttact tattttttg ccaaagctgt     180 aatggctgaa aattcttaca tttatttac attttagaa atgggcgtga aaaaaagcgc      240
gcgattatgt aaaatataaa gtgatagcgg taccattata ggtaagagag gaatgtacac    300

<210> SEQ ID NO 11
<211> LENGTH: 21
<212> TYPE: DNA
<213> ORGANISM: Artificial Sequence
<220> FEATURE:
<223> OTHER INFORMATION: Synthetic DNA

<400> SEQUENCE: 11
taacactaaa aggaggtaaa g                                                21
```